US00PP28955P2

(12) United States Plant Patent
Thompson

(10) Patent No.: US PP28,955 P2
(45) Date of Patent: Feb. 13, 2018

(54) JAPANESE HASKAP PLANT NAMED 'WILLA'

(50) Latin Name: ***Lonicera caerulea* var. *emphyllocalyx***
Varietal Denomination: Willa

(71) Applicant: Maxine M. Thompson, Corvallis, OR (US)

(72) Inventor: Maxine M. Thompson, Corvallis, OR (US)

(73) Assignee: MAXINE M. THOMPSON TRUST, Corvallis, OR (US)

( * ) Notice: Subject to any disclaimer, the term of this patent is extended or adjusted under 35 U.S.C. 154(b) by 0 days.

(21) Appl. No.: 15/330,329

(22) Filed: Sep. 6, 2016

(51) Int. Cl.
*A01H 5/08* (2006.01)

(52) U.S. Cl.
USPC ..... Plt./156

(58) Field of Classification Search
USPC ..... Plt./156, 226
CPC ..... A01H 5/08; A01H 5/00
See application file for complete search history.

*Primary Examiner* — June Hwu
(74) *Attorney, Agent, or Firm* — Penny J. Aguirre

(57) ABSTRACT

A new cultivar of Japanese haskap plant named 'Willa' that is characterized by its an upright and spreading plant habit, its moderately vigorous plant habit, its fruit that mature mid-season, its fruit that are attractive in appearance with and oval-round in shape with some having a small neck at the attachment, its fruit that are firm in texture, large in size with a pleasant, mild taste with a BRIX of 15°, and its fruit attachment to the peduncle that is medium in strength; strong enough to prevent pre-harvest drop and yet loose enough to permit picking without tearing berry flesh.

2 Drawing Sheets

Botanical classification: *Lonicera caerulea* var. *emphyllocalyx*.
Variety denomination: 'Willa'.

CROSS REFERENCE TO RELATED APPLICATIONS

This application is co-pending with a U.S. Plant Patent Application filed derived from the same breeding program that is entitled Japanese haskap Plant Named 'Kuchi' (U.S. Plant patent application Ser. No. 14/757,020) and Japanese haskap Plant Named 'Kawai' (U.S. Plant patent application Ser. No. 14/757,023).

BACKGROUND OF THE INVENTION

The present invention relates to a new and distinct cultivar of *Lonicera caerulea* var. *emphyllocalyx* and will be referred to hereafter by its cultivar name, 'Willa'. 'Willa' is a new cultivar of Japanese blue honeysuckle berry, also known as Japanese haskap, a plant grown for its fruit that is marketed as fresh and frozen fruit and processed food products.

The new Invention arose from an ongoing controlled breeding program in Corvallis, Oreg. with the planting of seeds collected in 2000 from several berry farms in Hokkaido, Japan. The objectives of the breeding program are to develop superior cultivars of this early ripening berry plant that could be grown in moderate to colder climates combined with an upright spreading plant habit and fruit that are large in size, attractive in appearance, firm texture, easy to pick, pleasant taste, and berries with a medium to strong attachment to the berry peduncle and a range of fruit maturity spreading throughout the harvest season with a high yield rate.

This new cultivar, 'Willa', arose from a controlled cross made in 2004 between unnamed and unpatented proprietary seedlings from the Inventor's breeding program; selection No. 19-27 as the female parent and selection No. 20-04 as the male parent. The Inventor selected 'Willa' in 2008 as a single unique plant from amongst the seedlings that resulted from the above cross.

Asexual propagation of the new cultivar was first accomplished by the Inventor by hardwood stem cuttings in 2008 in Corvallis, Oreg. Asexual propagation by hardwood and softwood cuttings has determined that the characteristics of the new cultivar are stable and are reproduced true to type in successive generations.

SUMMARY OF THE INVENTION

The following traits have been repeatedly observed and represent the characteristics of the new cultivar as grown outdoors in a trial plot for eight years in Corvallis, Oreg. These attributes in combination distinguish 'Willa' as a unique cultivar of Japanese haskap.

1. 'Willa' exhibits an upright and spreading plant habit.
2. 'Willa' exhibits a moderately vigorous growth habit.
3. 'Willa' exhibits fruit that mature mid-season.
4. 'Willa' exhibits fruit that are attractive in appearance and oval-round in shape with some having a small neck at the attachment.
5. 'Willa' exhibits fruit that are firm in texture and are large in size.
6. 'Willa' exhibits pleasant, mild tasting fruit with a BRIX of 15°.
7. 'Willa' exhibits fruit attachment to the peduncle that is medium in strength; strong enough to prevent pre-harvest drop and yet loose enough to permit picking without tearing berry flesh.

The female parent differs from 'Willa' in having fruit that is smaller in size with a softer texture, cylindrical shape, slightly red color and a flavor that is more tart. The male parent differs from 'Willa' in having fruit that is smaller in size, oval in shape, softer in texture and a harvest date 5 days earlier. 'Willa' can be most closely compared to the cultivars 'Kuchi' and 'Kawai'. 'Kuchi' differs from 'Willa' in having fruit that is cylindrical in shape, a more tart taste (BRIX 12°) and in having a more upright growth habit. 'Kawai' differs from 'Willa' in having smaller fruit that is quadrilateral in shape and in producing more berries per shoot.

BRIEF DESCRIPTION OF THE DRAWINGS

The accompanying colored photographs were taken of a 7 year-old plant as grown in research garden plot in Corvallis, Oreg.

The photograph in FIG. 1 provides a view of the plant habit of 'Willa'.

Figure 1:
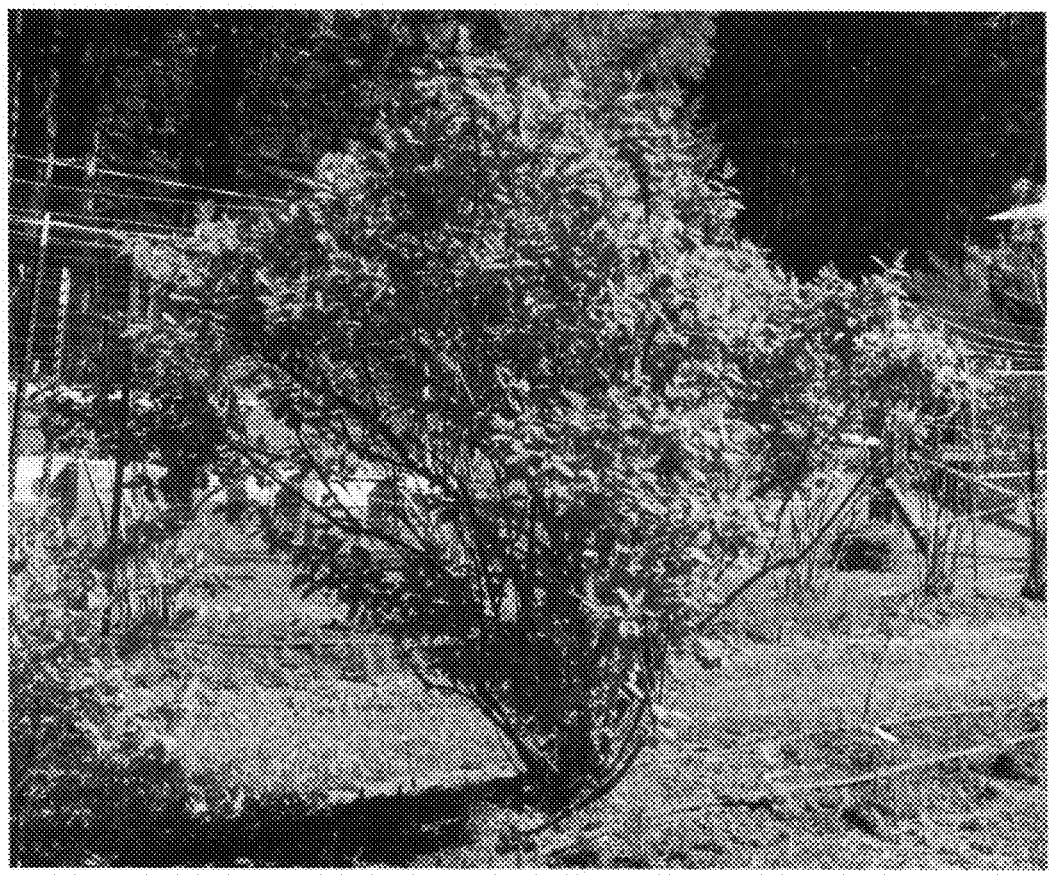
Figure 2:
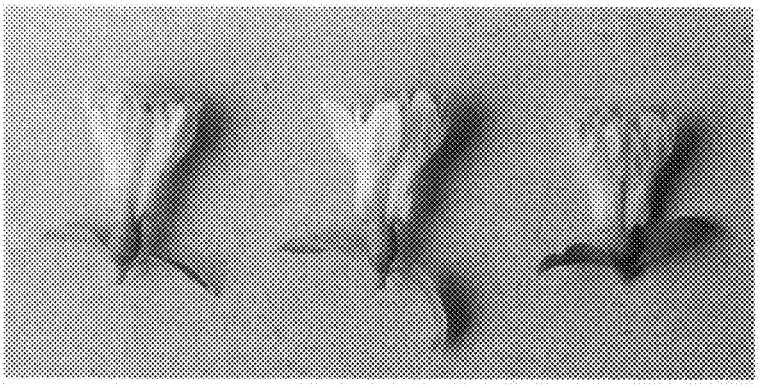

The photograph in FIG. 2 provides a close-up view of the flowers of 'Willa'.

Figure 3:
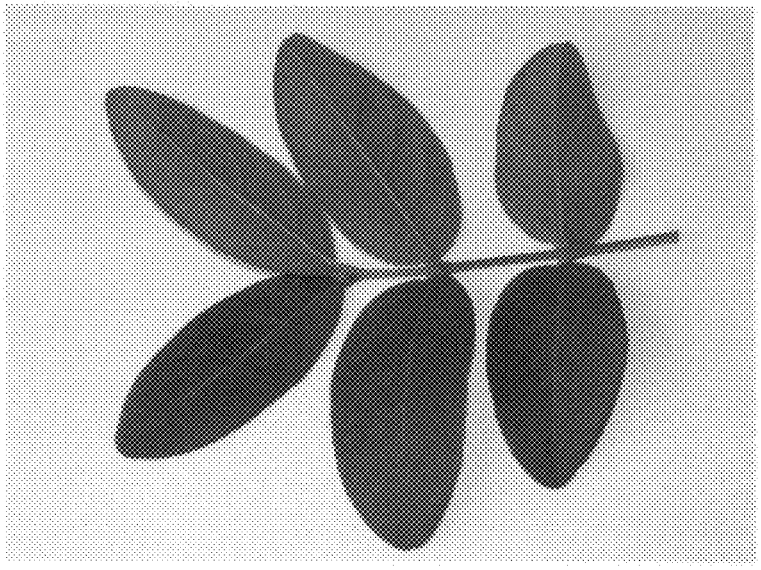

The photograph in FIG. 3 provides a close-up view of the leaves of 'Willa'.

Figure 4:
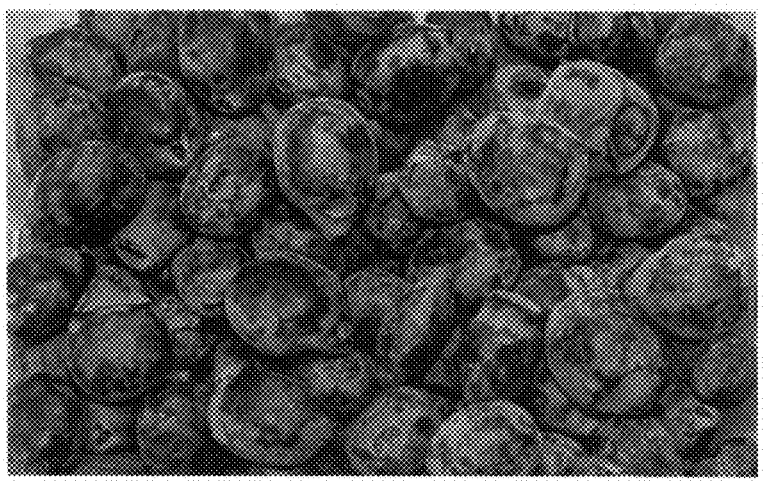

The photograph in FIG. 4 provides a view of the berries of 'Willa'.

The colors in the photographs may differ slightly from the color values cited in the detailed botanical description, which accurately describe the colors of the new Japanese haskap.

DETAILED BOTANICAL DESCRIPTION

The following is a detailed description of 7 year-old plants of the new Japanese haskap as grown outdoors on the Inventor's research plot in Corvallis, Oreg. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type*.—Deciduous shrub, fruit bearing.

*Plant habit*.—Upright and spreading.

*Plant size*.—Up to 1.7 m in height and 1.5 m in width (7 year-old plant in the landscape).

*Cold hardiness*.—At least hardy to U.S.D.A. Zone 3.

*Diseases and pests*.—No pests or disease problems have been observed.

*Root description*.—Fibrous.

*Propagation*.—Softwood and hardwood stem cuttings.

*Root development*.—Dormant cuttings stuck outside in early March are transplanted as rooted cuttings into 4×4×9 inch tubes in early May; when transplanted in the ground, plants reach 30.5 cm to 46 cm in height by fall.

*Growth rate*.—Medium to high vigor.

Dormant shoots:

*Density*.—Medium.

*New growth*.—137D in color, glabrous surface.

*One year-old shoots*.—22 to 40 cm (average of 31 cm) in length and 5 mm in diameter, surface is glabrous, 200D in color.

*Three year-old shoots*.—1 to 1.5 m in length (average of 1.3 m), 1.5 cm in diameter, surface exfoliating with inner bark 165A in color and outer bark 200D in color.

Foliage description:

*Leaf shape*.—Elliptic.

*Leaf division*.—Simple.

*Leaf base*.—Round.

*Leaf apex*.—Obtuse.

*Leaf venation*.—Pinnate, primarily match leaf coloration.

*Leaf margins*.—Entire.

*Leaf arrangement*.—Opposite.

*Leaf attachment*.—Petiolate.

*Leaf surface*.—Young and mature leaf upper and lower surface; glabrous.

*Leaf internode length*.—3 to 4 cm.

*Leaf size*.—6 to 7 cm in length and 3 to 4 cm in width.

*Leaf color*.—Young leaves upper and lower surface; 144A, mature leaves upper surface; 137B, mature leaves lower surface; 137D.

*Petioles*.—1 mm in length and width, 151A in color, glabrous surface, moderately strong.

*Stipules*.—Absent.

Inflorescence description:

*Blooming period*.—March 31$^{st}$ to April 19$^{th}$ in Corvallis, Oreg. (average of 3 years).

*Inflorescence type*.—Small 2-flowered cymule born in leaf axils of lowest 1 to 4 nodes on current years shoot.

*Inflorescence size*.—An average of 1.8 cm in length and 1.5 cm diameter.

*Flower buds*.—Mixed buds; flower buds are not visible as they are enclosed within the leaves of the bud.

*Flower fragrance*.—None.

*Lastingness of inflorescence*.—An average of 4 to 6 days.

*Flower type*.—Epigynous.

*Corolla form*.—Funnel-form, narrow at base, widening towards the apex, 5-lobed.

*Flower size*.—1.8 cm in length from base of ovary to tip of stigma, 3 mm in width at widest part at base, 5 mm near the apex.

*Flower number*.—3 to 4 flowers per shoot.

*Peduncles*.—2 mm in length, 1 mm in diameter, 137C in color, glabrous surface, moderately strong.

*Pedicels*.—Inconspicuous.

*Bracts*.—2, present at base of ovaries, lanceolate in shape, color upper surface 136C, color lower surface 136D, both surfaces glabrous, acute apex, acute base, 4 mm in width and 10 mm in length.

*Sepals*.—Fused with hypanthium.

*Petals*.—5, fused into a funnel form tube with apex and 5 lobes, corolla is 1.5 cm in length, 3 mm in width at base, 5 mm in width near apex, tube portion 6 mm in length, free portions are 4 mm in length and 6 mm in width, shape of free portions ovate-oblong with acute apex, inner surface glabrous, outside surface pilose, color inner surface 2C and outside 2B.

Reproductive organs:

*Gynoecium*.—1 pistil, an average of 1.8 cm in length, style 1.5 cm in length and 11D in color, stigma is about 1 mm in diameter and 130B in color, ovary is oval in shape, 4 mm in length and 3 mm in diameter and 137C in color.

*Androecium*.—5 stamens, adnate to inner surface of corolla tube, filaments are 11D in color and about 1 cm in length, anthers are 11A in color, pollen is very abundant in quantity and 11A in color with 98% acetocarmine stain.

*Compatibility*.—Self-incompatible.

Fruit description:

*Fruit development*.—60 days from mid-bloom to harvest.

*Harvest date*.—Average of June $5^{th}$ in Corvallis, Oreg.

*Fruit type*.—True berry, consists of 2 ovaries enclosed in fleshy bracts.

*Fruit shape*.—Round-round, some have a base that is slightly attenuated.

*Fruit size*.—Average of 1.8 to 2 cm in length and 1.4 to 1.5 cm in width.

*Fruit surface*.—Smooth with bloom.

*Fruit apex*.—Round.

*Fruit skin color*.—103A with bloom removed, 98D with bloom.

*Fruit flesh color*.—132D.

*Fruit firmness*.—Medium firm.

*Fruit brix*.—15°.

*Fruit juiciness*.—Medium.

*Fruit taste*.—Sweet and tart.

*Fruit weight*.—An average of 2.0 g.

*Peduncle*.—8 to 10 mm in length.

*Pedicel-berry scar*.—Dry.

*Fruit attachment strength*.—Medium; strong enough to avoid pre-harvest drop and loose enough to pick without tearing berry flesh.

*Post-harvest*.—Berries maintain their appearance, firmness and taste for at least 2 weeks in cold storage at 33° F. to 35° F.

*Fruit yield*.—Medium high, 2.3 lbs. on a seven year-old plant.

*Market uses*.—Fresh, frozen, dried fruit and particularly suited for processed products.

*Seed*.—Average of 11 seeds per fruit, seeds; lenticular in shape when dry, dry weight size is 138 mg/100 seeds, N199C in color.

It is claimed:

1. A new and distinct cultivar of Japanese haskap plant named 'Willa' as herein illustrated and described.

* * * * *